US011447462B2

(12) United States Patent
Alcarazo Velasco et al.

(10) Patent No.: US 11,447,462 B2
(45) Date of Patent: Sep. 20, 2022

(54) DIBENZOTHIOPHENE SALT AS ALKYNYLATING AND CYANATING AGENT

(71) Applicant: GEORG-AUGUST-UNIVERSITÄT GÖTTINGEN STIFTUNG ÖFFENTLICHEN RECHTS, Göttingen (DE)

(72) Inventors: Manuel Alcarazo Velasco, Göttingen (DE); Christopher Golz, Göttingen (DE); Bernd Waldecker, Göttingen (DE); Xiangdong Li, Göttingen (DE)

(73) Assignee: GEORG-AUGUST-UNIVERSITÄT GÖTTINGEN STIFTUNG ÖFFENTLICHEN RECHTS, Göttingen (DE)

( * ) Notice: Subject to any disclaimer, the term of this patent is extended or adjusted under 35 U.S.C. 154(b) by 0 days.

(21) Appl. No.: 17/254,774

(22) PCT Filed: Jul. 11, 2019

(86) PCT No.: PCT/EP2019/068711
§ 371 (c)(1),
(2) Date: Dec. 21, 2020

(87) PCT Pub. No.: WO2020/011935
PCT Pub. Date: Jan. 16, 2020

(65) Prior Publication Data
US 2021/0261519 A1 Aug. 26, 2021

(30) Foreign Application Priority Data
Jul. 12, 2018 (DE) .................... 10 2018 211 606.7

(51) Int. Cl.
C07D 333/76 (2006.01)
C07B 37/02 (2006.01)
C07B 43/08 (2006.01)

(52) U.S. Cl.
CPC ............ *C07D 333/76* (2013.01); *C07B 37/02* (2013.01); *C07B 43/08* (2013.01)

(58) Field of Classification Search
CPC .................................................. C07D 333/76
See application file for complete search history.

(56) References Cited

FOREIGN PATENT DOCUMENTS

WO   WO 2016/087879 A1   6/2016
WO   WO 2016/107578 A1   7/2016
WO   WO 2017/001245 A1   1/2017

OTHER PUBLICATIONS

Alcarazo, "Stellungnahme zur Erwiderung auf den Recherchebericht zur Patentanmeldung DE102018211606A1," Jun. 8, 2021, 1 page total.
Li et al., "5-(Diarylimino)- and 5-(sulfoximido) dibenzothiophenium triflates: syntheses and applications as electrophilic aminating reagents," Organic & Biomolecular Chemistry, vol. 19, 2021, pp. 2941-2948, 8 pages total.
Xu et al., "Site-Selective Late-Stage Aromatic [18F]Fluorination via Aryl Sulfonium Salts," Angewandte Chemie International Edition, vol. 59, 2020, pp. 1956-1960, 5 pages total.
Aukland et al., "An Interrupted Pummerer/Nickel-Catalysed Cross-Coupling Sequence." Angew. Chem. Int. Ed., vol. 57, No. 31, 2018, pp. 9785-9789.
Ecole Polytechnique, "Benziodoxoles Stability Data," Laboratory of Catalysis and Organic Synthesis LCSO, https://lcso.epfl.ch/research/bxstabilitydata/, Jun. 25, 2018, pp. 1-5.
Ecole Polytechnique, "Electrophilic Alkynylation," Laboratory of Catalysis and Organic Synthesis LCSO, https://www.epfl.ch/labs/lcso/research/hypervalentiodine/, Jun. 25, 2018, pp. 1-13.
Fascione et al., "Mechanistic Studies on a Sulfoxide Transfer Reaction Mediated by Diphenyl Sulfoxide/Triflic Anhydride," Chem. Eur. J., vol. 18, 2012 (Published online: Jan. 31, 2012), 2987-2997.
German Examination Report, dated Mar. 8, 2019, for German Application No. 102018211606.7.
Höfer et al., "Photochemistry and Initiation Behavior of Phenylethynyl Onium Salts as Cationic Photoinitiators," Journal of Polymer Science: Part A: Polymer Chemistry, vol. 47, 2009. pp. 3419-3430.
International Search Report and Written Opinion of the International Searching Authority, dated Oct. 8, 2019, for International Application No. PCT/EP2019/068711, with an English translation of the International Search Report.
Kumar et al., "Chemoselective Oxidation of Sulfides to Sulfoxides Using N-t-Butyl-N-chlorocyanamide," Chemistry Letters, vol. 34, No. 9, 2005 (Published on the web Advance View, Jul. 30, 2005), pp. 1230-1231.
Li et al., "5 (Cyano)dibenzothiophenium Triflate: A Sulfur-Based Reagent for Electrophilic Cyanation and Cyanocyclizations," Angew. Chem. Int. Ed., vol. 58, 2019. pp. 9496-9500.
Ochiai et al., "Synthesis of 1-alkynyl(diphenyl)onium Salts of Group 16 Elements via Heteroatom Transfer Reaction of 1-alkynyl(phenyl)lamda$^3$-iodanes." Org. Biomol. Chem., vol. 1, 2003 (First published as an Advance Article on the web on Mar. 27, 2003), pp. 1517-1521.
Simkó et al., "Sulfonium Salts as Alkylating Agents for Palladium-Catalyzed Direct Ortho Alkylation of Anilides and Aromatic Ureas," Organic Letters, vol. 20, No. 3, 2018 (Published: Jan. 12, 2018), pp. 676-679.
Talavera et al., "Dihalo(imidazolium)sulfuranes: A Versatile Platform for the Synthesis of New Electrophilic Group-Transfer Reagents," J. Am. Chem. Soc., vol. 137, 2015, pp. 8704-8707 (total 5 pages).

(Continued)

*Primary Examiner* — Golam M Shameem
(74) *Attorney, Agent, or Firm* — Birch, Stewart, Kolasch & Birch, LLP

(57) ABSTRACT

The present invention describes a new alkynylation and cyanation agent, as well as its preparation and use to introduce nitrile (cyano) or alkyne groups into chemical target molecules by means of an electrophilic reaction. To enable an electrophilic reaction, the chemical backbone of dibenzothiophene was used.

14 Claims, 6 Drawing Sheets

(56) References Cited

OTHER PUBLICATIONS

Waldecker et al., "5-(Alkynyl)dibenzothiophenium Triflates: Sulfur-Based Reagents for Electrophilic Alkynylation," Angew. Chem. Int. Ed., vol. 57, 2018, pp. 12538-12542.

Zhdankin et al., "1-(Organosulfonyloxy)-3(1H)-1,2-benziodoxoles: Preparation and Reactions with Alkynyltrimethylsilanes," J. Org. Chem. 1996, vol. 61, No. 19, pp. 6547-6551.

DIBENZOTHIOPHENE SALT AS ALKYNYLATING AND CYANATING AGENT

The present invention describes a new alkynylation and cyanation agent, as well as its preparation and use to introduce nitrile (cyano) or alkyne groups into chemical target molecules by means of an electrophilic reaction. To enable an electrophilic reaction, the chemical backbone of dibenzothiophene was used.

STATE OF THE ART

The present invention describes a novel alkynylation and cyanation agent and its synthesis. Alkynes are essential building blocks of synthetic and medicinal chemistry, materials science and chemical biology. Due to their linear geometry and electronic properties they are important structural elements in supramolecular aggregates and organic materials. The unique reactivity of the triple bond also makes them ideal precursors for other functional groups, not only in classical chemistry but also for biological and medical applications (e.g. ADCs). The development of new methods to bind these reactive functional groups is therefore an important research area in organic chemistry. Similarly, the introduction of nitrile (cyano) groups, i.e. CN groups, into organic compounds is of great importance.

The transfer of terminal alkynes is one of the most successful approaches to introduce triple bonds into organic molecules. This field has been mainly dominated by the use of acetylide anions or their equivalents as nucleophiles due to their easy formation. Processes such as the so-called Sonogashira coupling and the addition of alkynes to carbonyls are very reliable and are often used in synthetic chemistry. However, the disadvantage of this approach is that alkynes can only be introduced into the electrophilic positions of molecules.

A first described electrophilic alkynylation agent utilizes the chemical properties of ethinylbenziodoxolone (EBX) reagents for the gold-catalyzed alkynylation of indoles, pyrroles, thiophenes and furans. The cyclic hypervalent iodine reagent (TIPS-EBX) was first described by Zhdankin (Zhdankin et al.: "1-(Organosulfonyloxy)-3(1H)-1,2-benziodoxoles: Preparation and Reactions with Alkynyltrimethylsilanes", J. Org. Chem 1996, 61, 6547). However, the developed C—H-alkynylation is only suitable for the most electron-rich position of heterocycles. Triple bonds at other positions of aromatic rings are not possible. EBX compounds also show strong exothermic decompositions when heated and some of them are potentially explosive. On the other hand, reducing the explosivity can lead to a reduction of the desired reactivity.

WO 2017/001245 A1 (Alcarazo et al.) describes substituted imidazolium sulfurans and their use for the transfer of a CN group or an alkyne group (electrophilic cyanation or alkynylation). Here an imidazolium sulfurane is described as the backbone of an electrophilic reagent. The corresponding scientific publication is by Talavera et al ("Dihalo(imidazolium)sulfuranes: A Versatile Platform for the Synthesis of New Electrophilic Group-Transfer Reagents", J. Am. Chem. Soc. 2015, 137, 8704-8707).

WO 2016/107578 A1 (Umemoto et al.) describes a halogenated S-(perfluoroalkyl) dibenzothiophenium salt as a new, reactive and industrially useful reagent for perfluoroalkylation of organic compounds. The reagent is also known as Umemoto's reagent. The use in connection with the transfer of a CN or alkyne group or for the preparation of a CN or alkyne transferring agent is not disclosed.

Furthermore, WO 2016/087879 A1 (Slattery et al.) describes a new process for the fluorination of organic compounds (electrophilic fluorination). As electrophilic trifluoromethylation reagents the Umemotos reagent is also disclosed. The use in connection with the transfer of a CN or alkyne group is not disclosed.

It is therefore a task of the present invention to provide alternative reagents for the transfer of nitrile (cyano) or alkyne groups with an improved safety profile, which are characterized by simple synthesis and allow a wide range of applications with good yields. In particular, it should be possible to tolerate different functional groups present in the target molecule.

SUMMARY OF THE INVENTION

The present invention describes a new alkynylation and cyanation agent, as well as its preparation and use to introduce alkyne or nitrite (cyano) groups into chemical target molecules by means of an electrophilic reaction. To enable electrophilic alkynylation, the chemical backbone of the dibenzothiophene or the so-called Umemoto agent was used. The synthesis of a salt produces a $[R-C\equiv C]^+$ cation as 'synthon', which can undergo electrophilic substitution.

The invention thus concerns a salt containing a compound of formula I or II (i.e. a cation of the compound of formula I or II):

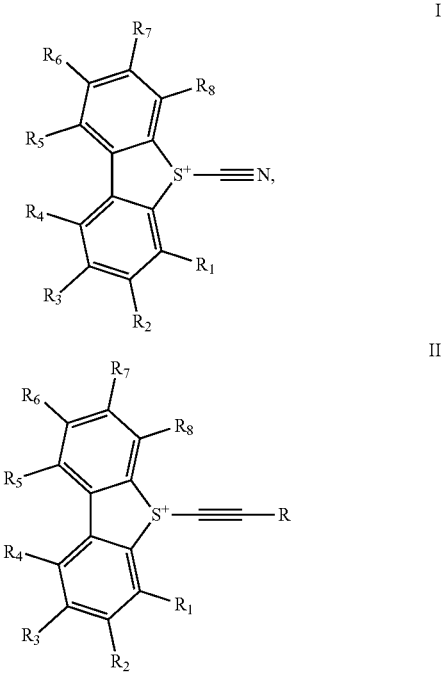

wherein $R_1$-$R_8$ are independently selected from the group consisting of: H, Cl, Br, F, I, $NO_2$, O—$C_{1-6}$ alkyl, $SO_3^-$, $C_{1-6}$ alkyl, $C_{6-12}$ aryl, O—$C_{6-12}$ aryl, $C_{6-12}$ heteroaryl, CN, COOR*, where R* =H, $C_{1-6}$ alkyl, $C_{6-12}$ aryl, and $COO^-$;

wherein R in Formula II is selected from the group consisting of: H, OMe, silyl groups and organic compounds bonded via a carbon atom. The anion of the salt is called "X" and preferably has one negative charge.

Furthermore, the invention relates to the use of the compound of formula

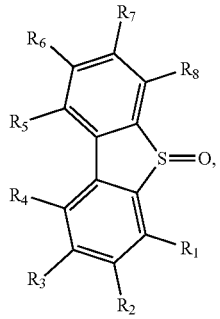

III as an intermediate stage in cyanation or alkynylation reactions. Also included is the use of formula III for the preparation of the salt of the invention, and cyanation or alkynylation reactions using the salt of formula I and II.

The invention also provides for the production of the salt according to the invention and its use in cyanation or alkynylation reactions.

DETAILED DESCRIPTION OF THE INVENTION

The present invention relates to an electrophilic alkynylation and cyanation agent, which is a dibenzothiophene salt of a nitrile (cyano) or alkyne compound. Essential for a successful commercial application is the easy producibility of the compound in large quantities.

In the context of the invention, it was determined that the thioimidazolone framework is not well suited for the application according to the invention, since highly nucleophilic Grignard reagents lead to undesired thioalkylation. Thus, it was found to be difficult to provide an electrophilic $[R-C\equiv C]^+$ cation that is stable and readily synthetically accessible and allows a high yield of the electrophilic reaction at the desired position in the target molecule. Surprisingly, however, the basic structure of dibenzothiophene was found to be very advantageous.

The advantages of the alkynylation and cyanation agent of the invention (herein also referred to as "agent of the invention" or "reagent of the invention") are that it is easy to produce and suitable for a wide range of substrates. For example, it can react as an electrophile by electrophilic substitution with nucleophilic thiols, amines, and activated methylenes. In addition, the agent does not have the disadvantage of being attacked by nucleophiles at undesirable sites, which would not lead to an alkylation or cyanation reaction. Here, nucleophiles attack the alkynyldibenzothiophene salts of the invention at the α and β-carbon atoms and produce the desired alkynes by eliminating the dibenzothiophene moiety. Advantageously, the agent according to the invention tolerates many different functional groups (e.g. ketones, esters, amides, halogens, ethers, nitro and cyano) and thus enables versatile applications for the production of complex compounds. It thus enables a broader range of applications compared to electrophilic alkynylation reagents based on imidazolesulfuran as the backbone.

A further advantage are the good to very good yields in the production of the agent of invention, as well as its use in alkynylation and cyanation reactions according to the invention. The synthesis of exemplary novel alkynylation reagents (dibenzothiophene-alkynyl-R) was between 70 and 97%. The yields of the subsequent alkynylation reactions of various exemplary organic molecules were between 60 and 91%. Furthermore, unlike other known compounds (e.g. EBZ), the agent according to the invention is not explosive. The decomposition energy of 3a (see FIG. 1) was determined by differential scanning calorimety (DSC) to be 449 J/g, which is more than 100 J/g lower than that of R-EBX.

As a commercial application of the novel electrophilic alkynylation and cyanation agent, in particular synthetic and medicinal chemistry should be mentioned.

The present invention thus concerns the following embodiments

1. Salt containing a compound of formula I or II:

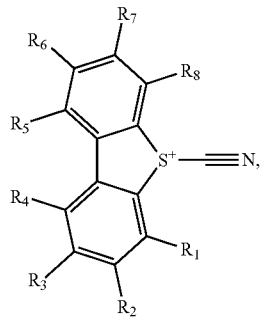

I

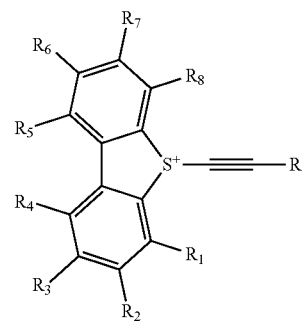

II wherein $R_1$-$R_8$ are independently selected from the group consisting of: H, Cl, Br, F, I, $NO_2$, O—$C_{1-6}$ alkyl, $SO_3^-$, $C_{1-6}$ alkyl, $C_{6-12}$ aryl, O—$C_{6-12}$ aryl, $C_{6-12}$ heteroaryl, CN, COOR*, where R* =H, $C_{1-6}$ alkyl, $C_{6-12}$ aryl, and COO$^-$; bevorzugt, H, Cl, Br, F, I, $NO_2$, further preferred H;

wherein R in Formula II is selected from the group consisting of: H, OMe, silyl groups and organic compounds bonded via a carbon atom.

In one embodiment, $R_1$-$R_8$ in formula I and/or II are hydrogen:

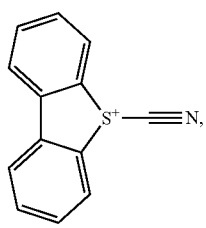

I

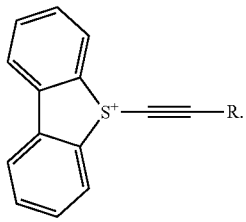

2. The salt according to embodiment 1, wherein the organic compounds are selected from the group consisting of: optionally substituted $C_{1-20}$ dialkyl ethers not bound via O; and optionally substituted linear; branched or cyclic $C_{1-20}$ hydrocarbon groups, optionally having one or more unsaturated bonds and optionally having one or more heteroatoms, preferably selected from O, N, and S, preferably the substituent(s) is (are) (a) fluorine atom(s) (e.g. fluorinated $C_{1-20}$ alkyl groups).

3. The salt according to embodiment 1 or 2, wherein R is an $R'_3$ silyl group, wherein the three R' substituents are independently selected from the group consisting of: optionally substituted linear, branched or cyclic $C_{1-12}$ hydrocarbon groups, optionally containing one or more unsaturated bonds and optionally one or more heteroatoms, preferably selected from O, N, and S, preferably the $R'_3$silyl group is selected from triisopropylsilyl, triethylsilyl, trimethylsilyl, tert-butyl dimethylsilyl and tert-butyl diphenylsilyl, preferably triisopropylsilyl.

4. The salt according to a previous embodiment, wherein R and the three R' substituents of the $R'_3$ silyl group are independently selected from the group consisting of: optionally substituted $C_{4-12}$ cycloalkenyl groups containing one or more unsaturated C—C double bonds (e.g. conjugated double bond systems), optionally substituted $C_{6-12}$ aryl groups, optionally substituted $C_{3-12}$ cycloalkyl groups, optionally substituted $C_{1-20}$ alkyl groups, optionally substituted $C_{1-20}$ alkenyl groups which have one or more unsaturated C—C double bonds (e.g. (e.g. conjugated double bond systems), optionally substituted $C_{1-20}$ alkynyl groups, optionally substituted $C_{1-20}$ heteroalkyl groups, optionally substituted $C_{1-20}$ heteroalkenyl groups, which have one or more unsaturated double bonds (e.g. conjugated double bond systems), optionally substituted $C_{1-20}$ heteroalkynyl groups, which optionally have one or more unsaturated double bonds (e.g. conjugated double bond systems), optionally substituted $C_{6-12}$ heteroaryl groups, optionally substituted $C_{3-12}$ heterocycloalkyl groups, optionally substituted $C_{3-12}$ heterocycloalkenyl groups, which have one or more unsaturated double bonds (e.g. (e.g. conjugated double bond systems),
preferably R and the three R' substituents are independently selected from the group consisting of optionally substituted $C_{6-12}$ heteroaryl groups, optionally substituted $C_{4-12}$ cycloalkenyl groups having one or more unsaturated C—C double bonds, optionally substituted $C_{6-12}$ heterocycloalkenyl groups having one or more unsaturated C—C double bonds, fluorinated $C_{1-12}$ alkyl groups (e.g. CHF, $CF_3$, $CHF_2$) and optionally substituted $C_{6-12}$aryl groups (e.g. halogenated, in particular fluorinated, aromatic groups), further preferred R is selected from fluorinated $C_{1-12}$ alkyl groups (e.g. CHF, $CF_3$, $CHF_2$) and halogenated, in particular fluorinated, $C_{6-12}$ aryl groups.

In the context of "$C_{3-12}$ cycloalkyl groups", "$C_{1-20}$ alkyl groups", "$C_{1-20}$ alkenyl groups", "$C_{1-20}$ alkynyl groups", "$C_{1-20}$ heteroalkyl groups", "$C_{1-20}$ heteroalkenyl groups", "$C_{1-20}$ heteroalkynyl groups", "$C_{6-12}$ heteroaryl groups", "$C_{3-12}$ heterocycloalkyl groups", "$C_{3-12}$ heterocycloalkenyl groups", "$C_{6-12}$ cycloalkenyl groups", etc., the number of carbon atoms does not refer to the optionally present substituents, but only to the basic structure mentioned.

Herein the term "optionally substituted" preferably means that substituents are present, preferably 1-3 substituents, wherein the substituents are selected from the group consisting of halogen, preferably F, $CF_3$, =O, —$NO_2$, —SH, —CN, —OR", —R", —SR", —COR", —COOR", —$NH_2$, —NHR", —N(R")—R"—NH—$C_{1-6}$ alkyl, —N($C_{1-6}$ alkyl)$_2$, —NH($C_{1-6}$ alkyl), halogen-substituted $C_{1-6}$R", $C_{1-6}$R", wherein R" is $C_{1-10}$-alkyl, $C_{6-12}$-aryl, $C_{2-10}$ alkenyl, $C_{2-10}$ alkynyl, $C_{7-10}$ alkylenyl, $C_{7-10}$ arylalkyl, $C_{2-10}$ heterocycloalkyl, or $C_{2-10}$ alkylheterocyclyl, and wherein the substituents themselves may also be substituted;
and wherein the term "alkyl", "alkenyl", "alkynyl" comprises linear, branched and cyclic, preferably linear, alkyl, alkenyl, alkynyl chains and mixed variants thereof;
and wherein the term "hetero" in "heteroaryl", "heterocycloalkyl", "heterocycloalkenyl" and "heteroalkyl" means that one or more heteroatoms selected from O, N, P and S are present.

Preferably the number of halogen atoms in $R_1$-$R_8$ is 1-5, more preferably 1-3.

5. The salt according to a previous embodiment, where $R_1$-$R_8$ are independently selected from the group consisting of: H, $CH_3$ and F.

6. The salt according to a previous embodiment, wherein the compound of formula I or formula II represents the cation and the anion is "X" and X is preferably selected from the group consisting of ions having one negative charge: triflate (TfO$^-$), perchlorates, nitrate, $Tf_2N$, [{3,5-$(CF_3)_2C_6H_3$}$_4$B]$^-$, PF6$^-$, BF4$^-$, B($C_6F_5$)$_4^-$, BF4$^-$, BR*$_4$, wherein R*=optionally substituted $C_{1-6}$ alkyl, optionally substituted $C_{6-12}$ aryl, especially F, and $CF_3$, and/or CN substituted), 1-Carba-closo-dodecaborate(1-) and corresponding compounds, HC($SO_2CF_3$)2$^-$ and corresponding compounds, $C_{60}^-$, halides, $PF_6^-$, $SbF_6^-$, $Sb_2F_{11}^-$ and further antimonate compounds, fluorinated alkoxyaluminates, tosylates, preferably triflate (TfO–) represents the anion. In general, all weakly bound counter ions are suitable.

Phenylethinyl-Onium salts as photoinitiators with PF6$^-$-, OTf$^-$-oder BF4$^-$-counterions are known (Ochiai, et al., *Org. Biomol. Chem.* 2003, 1, 1517-1521; Höfer et al., *J. Pol. Sci; Part A: Pol. Chem.* 2009, 47, 3419-3430).

7. The salt according to a previous embodiment wherein R is selected from toluene, para-methoxyphenyl, naphthyl, triisopropylsilyl, triethylsilyl, trimethylsilyl, tert-butyl dimethylsilyl and tert-butyl diphenylsilyl, preferably the salt contains the compound having the formula

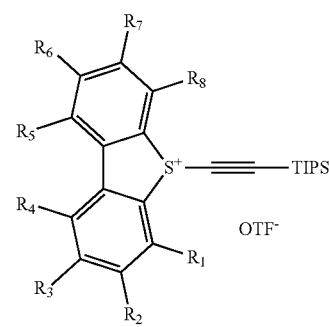

where TIPS stands for triisopropylsilyl. Preferably R is as shown in FIGS. 1, 3, 4, 5 and 6, where $R_1$-$R_8$ are preferably hydrogen.

8. Use of the compound of formula III

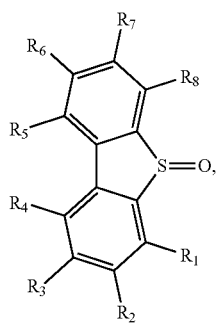

as an intermediate stage in cyanation or alkynylation reactions, preferably in a cyanation or alkynylation reaction as defined in one of the embodiments 10-17, wherein $R_1$-$R_8$ are defined as in one of the embodiments 1-7.

9. Use of the compound of formula III as defined in embodiment 8 for preparing the salt according to any one of embodiments 1-7.

10. A cyanation or alkynylation reaction comprising the steps
a) providing a salt containing the compound of formula I or II:

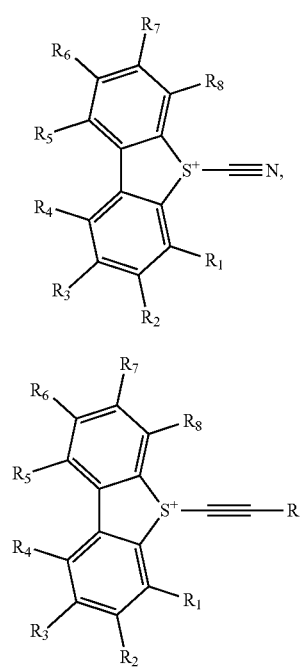

wherein $R_1$-$R_8$ are independently selected from the group consisting of: H, Cl, Br, F, I, $NO_2$, O—$C_{1-6}$-alkyl, $SO_3^-$, $C_{1-6}$-alkyl, $C_{6-12}$-aryl, O—$C_{6-12}$-aryl, $C_{6-12}$-heteroaryl, CN, COOR*, with R* =H, $C_{1-6}$-alkyl, $C_{6-12}$-aryl, and $COO^-$, preferably, H, Cl, Br, F, I, $NO_2$, further preferred H;

wherein R in Formula II is selected from the group consisting of: H, OMe, silyl groups and organic compounds bound through a carbon atom; and
b) reacting the salt with a nucleophile (Nu), optionally in the presence of a base or a Lewis acid, especially when using the compound of formula I, wherein —CN or the compound

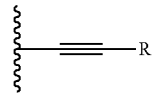

binds to the nucleophile.
Preferably R and R' are as defined in one of the previous embodiments.

11. The alkynylation reaction according to embodiment 10, where the nucleophile is Nu-H and reacts to

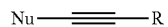

by cleaving off a hydrogen substituent, or the nucleophile contains at least one C—C double or triple bond and the alkyne group adds to the C—C double or triple bond.

12. The cyanation or alkynylation reaction according to one of embodiments 10-11, wherein dichloromethane, dichloroethane, acetonitrile, toluene or tetrahydrofuran, preferably dichloromethane, is used as solvent.

13. The cyanation or alkynylation reaction according to one of the embodiments 10-12, where the base is selected from the group consisting of tertiary amines (e.g. diisopropylamine) and inorganic salts (e.g. $Cs_2CO_3$, $K_3PO_4$, $K_2CO_3$), preferably $Cs_2CO_3$. Very strong bases like DBU seem to destroy the reagent. In principle, other poorly soluble inorganic bases could also be reactive.

The use of $Cs_2CO_3$ as a base is advantageous, since both aliphatic and aromatic thiols (with either electron-withdrawing or electron-donating substituents) can be reacted to the desired alkynylation products 7-16 (see FIG. 3).

14. Cyanation or alkynylation reaction according to any of embodiments 10-13, wherein step a) further comprises
a') providing a compound of formula III

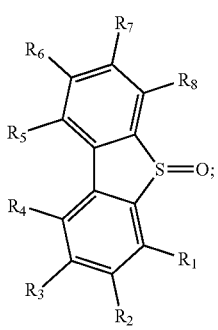

and reacting the compound of formula III to a salt containing the compound of formula I or II in two reaction steps:
Step 1) Reaction with an acid anhydride or an ester (preferably an ester of trifluoromethanesulfonic acid) preferably selected from the group consisting of: trifluoromethanesulfonic acid anhydride ($Tf_2O$), trimethylsilyl-OTf, trifluoroacetic acid anhydride, $Ac_2O$, and $Ts_2O$; and Step 2) subsequent reaction with a reagent selected from the group consisting of:

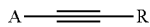

or A-CN, where A is selected from cations such as Na or K, ZnX, MgX, where X=halogen; TMS; $BR_2$ and $BR_3^-$, where R=optionally fluorinated O—$C_{1-6}$-alkyl, optionally fluorinated $C_{1-6}$-aryl, F or H, wherein an additional base is required when using H; preferably

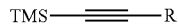

or TMS-CN.

In principle, the preferred acid anhydride is a compound that forms a stable, easily removable compound with the resulting TMS cation.

15. The cyanation or alkynylation reaction according to one of the embodiments 10-14, whereby step a') further comprises a") providing a compound of formula IV

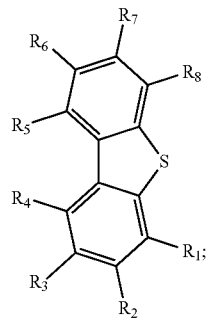

and reacting the compound of formula IV to the compound of formula III by reaction with an oxidizing agent, preferably an oxidizing agent selected from the group consisting of: trifluoromethanesulfonic add (Tf-OH)/$H_2O_2$, TfOOH, t-BuOOH, meta-chloroperbenzoic acid⁻, $O_2$/metal catalyst, PhIO, $Cl_2$, wherein $R_1$-$R_8$ are as defined in one of the embodiments 1-7.

16. The cyanation or alkynylation reaction according to one of the embodiments 10-15, wherein the nucleophile is selected from the group consisting of $R^x$—H, $R^x$—S—H, $R^x_2$—N—H, $R^x$—C(O)S—H, $R^x$—C(O)N$R^x$—H, sulfonamides ($R^x$—S(O)$_2$N$R^x$—H), doubly activated methylene compounds, amides, electron-rich aromatics (preferably nitrogen-containing heterocycles or substituted aryl groups with electron-donating substituents (+M effect), such as e.g. methoxy groups;

EXAMPLE

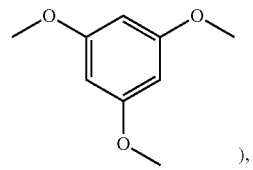

nitrogen-containing $C_{5-12}$ heterocycles (e.g. substituted indole and pyrrole derivatives), and $Ph_3P$, wherein $R^x$ is selected from the group consisting of: optionally substituted linear, branched or cyclic $C_{1-30}$ hydrocarbon groups optionally containing one or more unsaturated bonds and optionally one or more heteroatoms, preferably selected from O, N, P and S.

In one embodiment, the definition of $R^x$ corresponds to the definition of R or R', as stated herein at various places.

17. The cyanation or alkynylation reaction according to one of the embodiments 10-16, wherein the doubly activated methylene compound is a —CR$^x$H— or —$CH_2$-moiety activated with two functional groups selected from keto group, cyano group, amide group, sulfonamide group, ester group and $NO_2$ group.

e.g.:

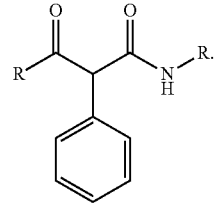

The activating functional group is located in a position of the activated methylene compound. Preferably, the activated methylene compound is a ketoester, a diketone, or a cyanoester, In one embodiment, the definition of $R^x$ corresponds to the definition of R or R', as indicated in various places herein.

18. Process for preparing a salt according to one of embodiments 1-7, comprising the steps of:

A) providing a compound of formula IV as defined in embodiment 15;

B) reacting the compound of formula IV to give the compound of formula III as defined in embodiment 15; and C) reacting the compound of formula III to a salt containing the compound of formula I or II in two reaction steps as defined in embodiment 14.

19. Use of a salt according to one of embodiments 1-7 in cyanation or alkynylation reactions, preferably cyanation or alkynylation reactions according to one of embodiments 10-17.

20 Use of a salt according to embodiment 19, wherein the salt is reacted as an electrophile with a nucleophile.

19 The use according to embodiment 18, where the nucleophile is defined as in embodiment 14.

Doubly activated methylene compounds, e.g. ketoester 18-24, diketone 25, or cyanoester 26, after reaction with the agent of the invention are shown in FIG. 3. These reactions can be performed at room temperature, although a better conversion can be achieved at 60° C. Similarly, sulfonamides ($R^x$—S(O)$_2$NR $R^x$—H) and bisamides 27-35, as well as Ph$_3$P 36 can be used.

Ketoesters can be represented by one of the following general formulas:

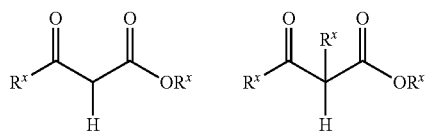

where all $R^x$ substituents are independently selected and defined as herein. Preferred are aryl and alkyl groups. In one embodiment, the definition of $R^x$ corresponds to the definition of R or R'.

Diketones can be represented by the following general formula

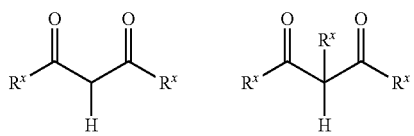

where all $R^x$ substituents are independently selected and defined as herein. Preferred are aryl and alkyl groups. In an embodiment, the definition of $R^x$ corresponds to the definition of R or R', as indicated in various places herein.

Cyanoesters can be represented by the following general formula:

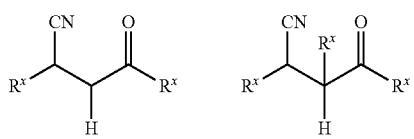

where all $R^x$ substituents are independently selected and defined as herein. Preferred are aryl and alkyl groups. In one embodiment, the definition of $R^x$ corresponds to the definition of R or R', as indicated in various places herein.

The production of dibenzothiophene and derivatives thereof used as starting materials in the present invention is also described in WO2016/107578.

The term "alkyl" as used herein refers to saturated or unsaturated straight chain/linear, branched, or cyclic hydrocarbon substituents, examples of alkyl groups include methyl, ethyl, propyl, butyl, pentyl, hexyl, octyl, decyl, isopropyl, sec-butyl, isobutyl, tert-butyl, isopentyl, vinyl, allyl, 1-butenyl, 2-butenyl, isobutenyl, and pentenyl.

The term "cycloalkyl", as used herein, refers to saturated or unsaturated, non-aromatic hydrocarbon cycles, which may consist of one, two or more rings. Examples include: cyclopropyl, cyclobutyl, cyclopentyl, cyclopentenyl, cyclopentadienyl, cyclohexyl, cyclohexonyl, etc.

The term "heteroalkyl" as used herein refers to saturated or unsaturated straight chain, cyclic or branched hydrocarbon substituents in which at least one carbon is replaced by a heteroatom. The heteroatoms are preferably selected from S, N, O, and P.

The term "aryl", as used herein, refers to aromatic substituents which may consist of one or more fused rings. Examples of aryl include: phenyl, naphthyl and anthracenyl.

The term "heteroaryl", as used herein, refers to aromatic substituents which may consist of one or more fused rings. In this case, at least one carbon atom of the aromatic R group is replaced by a heteroatom, especially S, N, O or P. Examples of heteroaryl groups include: pyridinyl, furanyl, pyrrolyl, triazolyl, pyrazolyl, imidazolyl, thiophenyl, indolyl, benzofuranyl, benzimidazolyl, indazolyl, benzotriazolyl, benzisoxazolyl, and quinolinyl.

The term "heterocycloalkyl" as used herein refers to saturated or unsaturated, non-aromatic cyclic hydrocarbon substituents, which may consist of one or more fused rings, where at least one carbon in one of the rings is replaced by a heteroatom, in particular S, N, O or P. Examples of heterocycloalkyls include tetrahydrofuranyl, pyrrolidinyl, piperidinyl, 1,4-dioxanyl, morpholinyl, piperazinyl, oxyzolidinyl, decahydroquinolinyl.

Based on these observations, it is assumed that the first step of the alkynyl transfer reaction is an alpha or beta attack on the triple bond.

B3LYP/6-31G*-calculations of 3a showed that the sulfur atom carries an almost complete positive charge (+0.946e).

Figure 3:
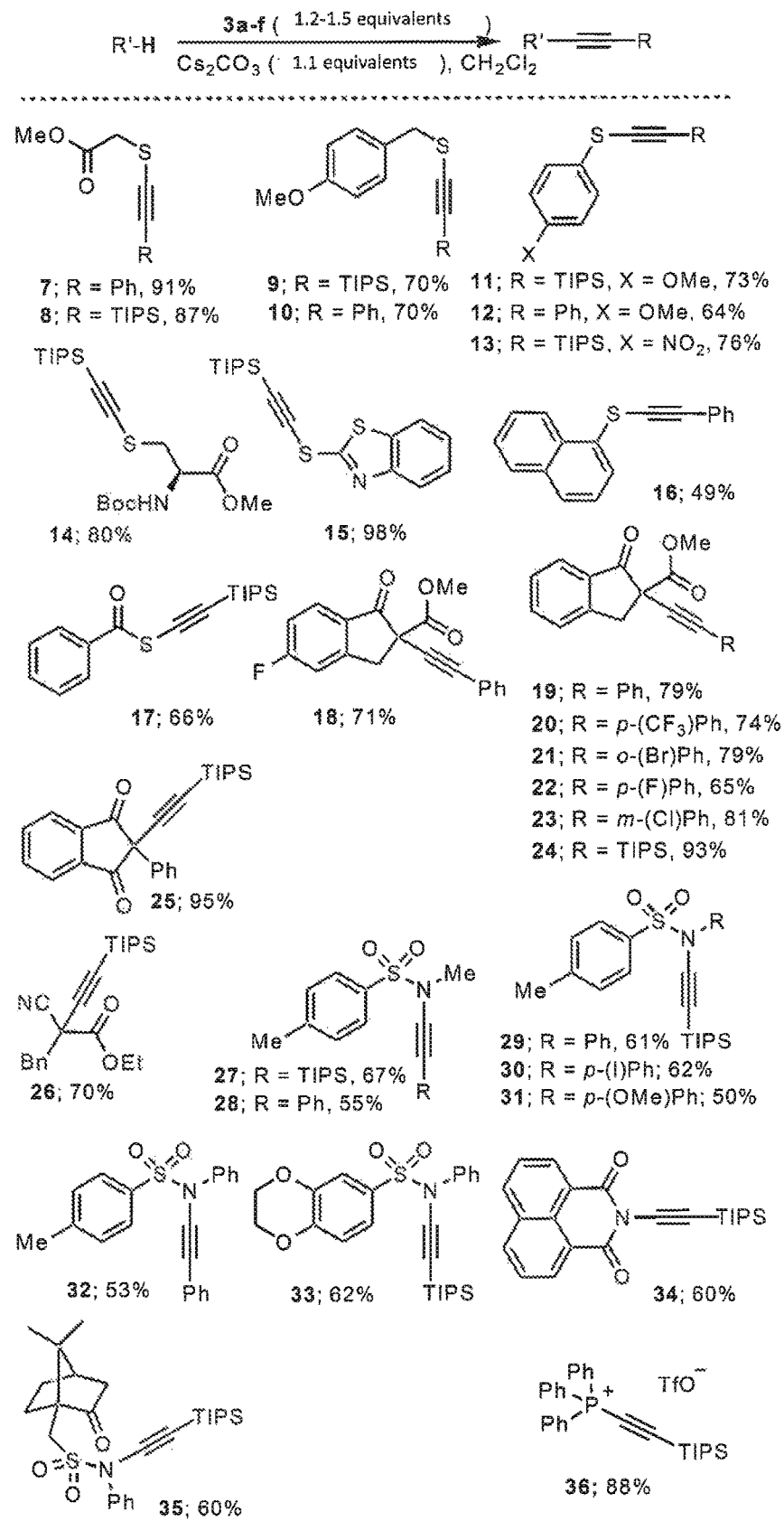

FIG. 3 shows the yields of alkynylation reactions with the alkynylating agent of the invention, using the following abbreviations: Ph=phenyl, TIPS=triIsopropylsilyl, OMe=OCH$_3$, Boc=tert-butyloxycarbonyl, TFO$^-$=triflate anion. For thiols and amides, the reactions were performed at room temperature, whereas methylene groups required 60° C. as reaction temperature. Reagents 3a-e and 3f were used in excess (1.5 equivalents and 1.2 equivalents, respectively). All reactions were quenched after 12 h. The yields refer to the isolated products.

Figure 1:
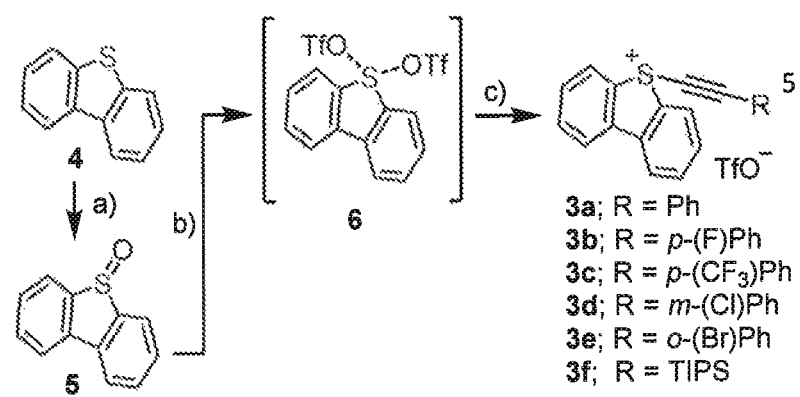
FIG. 1 shows the synthesis of alkynylating agents 3a-f according to the invention, using the following abbreviations Ph=phenyl, TIPS=triisopropylsilyl, and TFO$^-$=triflate anion. The following conditions were used: a) TfOH (trifluoromethanesulfonic acid), H$_2$O$_2$ (1.2 equivalents), 0→50° C., 76% (yield); b) Tf$_2$O (trifluoromethanesulfonic acid anhydride) (1 equivalent), −50° C., 1 h (not isolated); c) TMS-alkine (1 equivalent), 3a, 87%; 3b, 82%; 3c, 97%; 3d, 81%; 3e, 73%; 3f, 85%.
Figure 2:
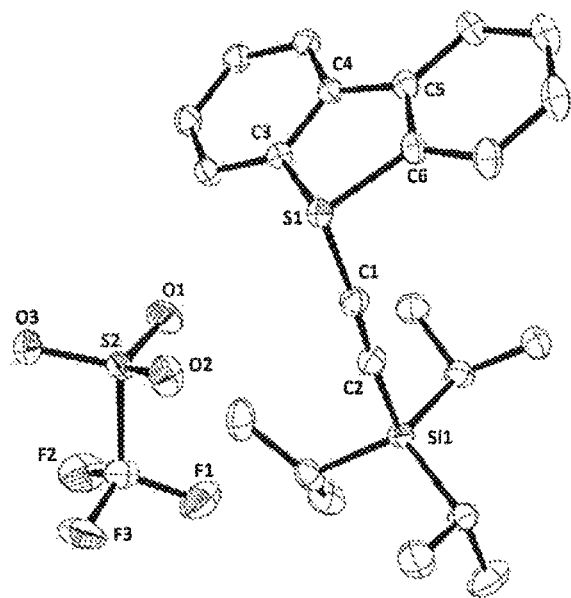
FIG. 2 shows an X-ray structure analysis of single crystals of 3a (lower figure) and 3f (upper figure). In both thiophene cations, the sulfur atom remains in the area defined by the dibenzothiophene skeleton. However, the C—S bond lengths within the aromatic fragment 1.7897(11) for S1-C6 in 3a and 1.7933(8) for S1-C3 in 3f are significantly longer than in dibenzothiophene (1.740 Å). This is a consequence of the substantial loss of aromaticity at the thiophene ring after binding of the alkynyl group and the subsequent reduction of S1-C3 and S1-C6 binding orders (Wiberg binding indices have been calculated but are not shown). Selected bond lengths [Å] and angles [degrees]; 3a: S1-C1, 1.6871(12); S1-C3, 1.7878(11); S1-C6, 1.7897(11); S1-O1, 3.157(1); O1-C1, 3.179(2); C3-S1-O1, 179.0(1); 3f: S1-C1, 1.6980(9); S1-C3, 1.7933(8); S1-C6, 1.7935(8); S1-O1, 2.972(1); O1-C1, 3.101(1); C6-S1-O1, 177.3(1).
Figure 2:
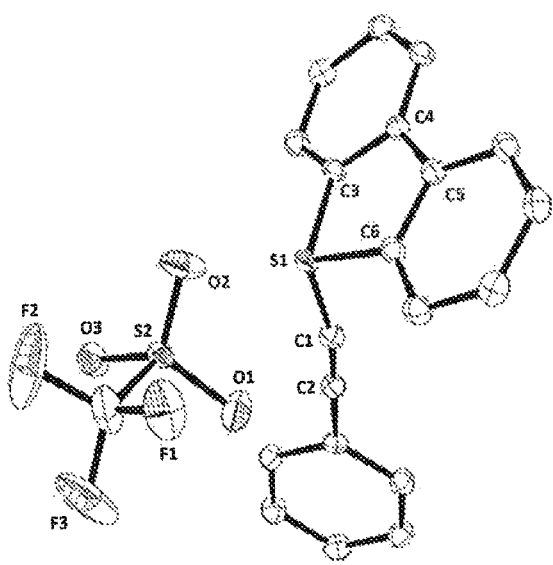
Figure 4:
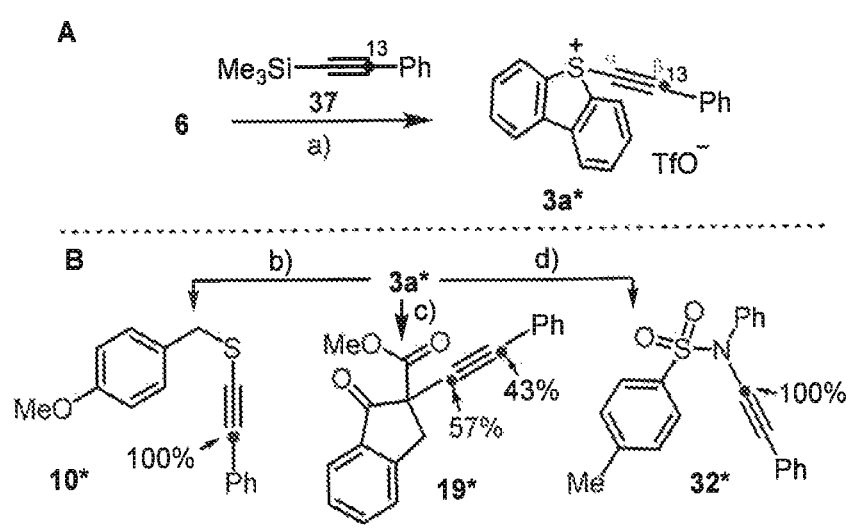

FIG. 4 shows the results of isotope labeling experiments. An isotope-labeled phenyl-substituted alkyne synthon 37 is reacted with bistriflate 6 (see FIG. 1) to form the agent 3a* of the invention and then reacted with p-(methoxy)benzylthiol, or a ketoester, or an N-phenyl-tosylamine, using the following conditions a) −50° C.→−15° C., 7 h, 90% yield; b) p-(methoxy)benzylthiol (1 equivalent), Cs$_2$CO$_3$ (1 equivalent), CH$_2$Cl$_2$, room temperature; c) ketoester (1 equivalent), Cs$_2$CO$_3$ (1 equivalent), CH$_2$Cl$_2$, 60° C.; d) N-phenyl-tosylamine (1 equivalent), Cs$_2$CO$_3$ (1 equivalent), CH$_2$Cl$_2$, room temperature.

The analysis of compound 10* shows complete retention of the $^{13}$C at its original position in 3a*. The result is either consistent with a direct attack of the thiol at the a position of 3a* and simultaneous elimination of dibenzothiophene, or with the reaction of the S nucleophile at the β-carbon, followed by exclusive 1,2 migration of the thio group. The NMR spectrum of aminoalkine 32* shows that the labeled carbon atom is bound to the nitrogen atom. This is only consistent with an attack of the amide at the β-position of alkyne 3a, followed by exclusive 1,2-phenyl group migration. The nucleophilic attack at the β-position can also explain the mixed products 19*, since the migration ability of phenyl and tertiary alkyl radicals is known to be comparable. However, the coexistence of a and 6-attack pathways cannot be excluded.

Figure 5:
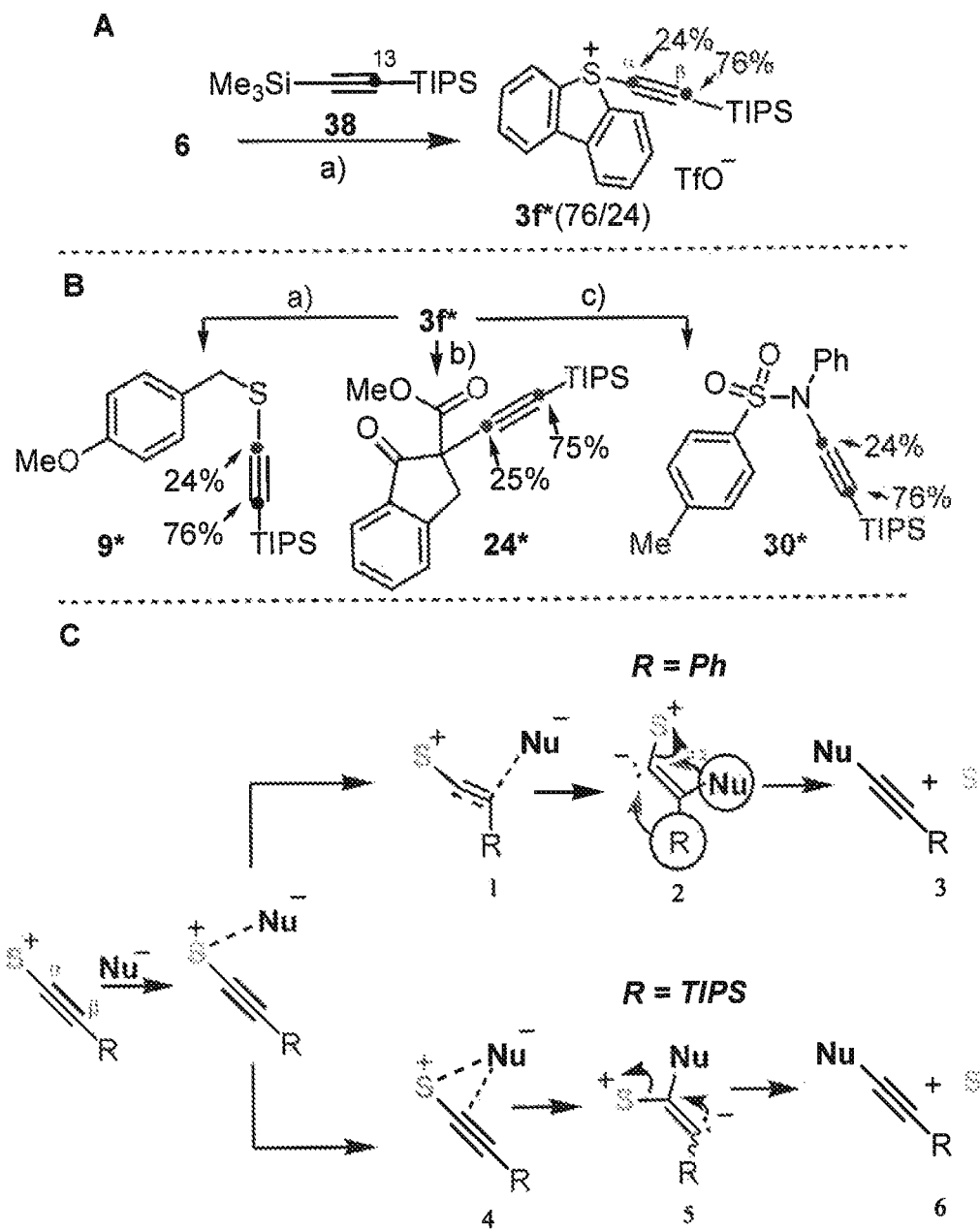

FIG. 5 shows the results of isotope labeling experiments. An isotope-labeled TIPS-substituted alkyne synthon 38 is reacted with bistriflate 6 (see FIG. 1) to form the agent 3f* according to the invention and then reacted with p-(methoxy)benzylthiol, or a ketoester, or an N-phenyl-tosylamine, using the following conditions a) −50° C.→0° C., 7 h, 85% yield; b) p-(methoxy)benzylthiol (1 equivalent), Cs$_2$CO$_3$ (1 equivalent), CH$_2$Cl$_2$, room temperature; c) ketoester (1 equivalent), Cs$_2$CO$_3$ (1 equivalent), CH$_2$Cl$_2$, 60° C.; d) N-phenyl-tosylamine (1 equivalent), Cs$_2$CO$_3$ (1 equivalent), CH$_2$Cl$_2$, room temperature. In FIG. 5c, "S" stands for dibenzothiophene. The labeling is as follows: 1=β attack; 2=β addition product; 3=S elimination step +1,2 shift; 4=α attack; 5=α addition product; 6=S elimination step.

The TIPS group was selected because 1,2-migration of silicon moieties in vinylcarbenoids is known to be significantly faster than that of alkyl- or sulfur-based substituents. 3f* was obtained and used as a 3:1 mixture of the isotopomers. In the reaction of 3f* with p-(methoxy)benzylthiol to obtain 9, the main product obtained was that in which the more strongly labeled carbon atom was still attached to the silicon moiety. This result means that for sulfur-based nucleophiles, the most likely is an a attack. The same observations were made for C- or N-based nucleophiles.

Figure 6A:
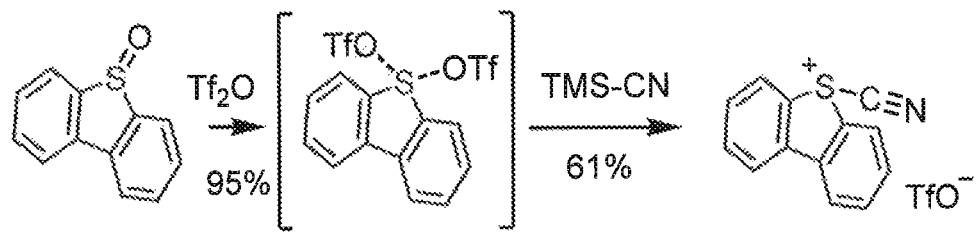

FIG. 6a shows the synthesis of a cyanation agent according to the invention, using the following abbreviations: TMS=trimethylsilyl, and TF$_2$O=trifluoromethanesulfonic acid anhydride, and TfO$^-$=triflate. The following synthesis was performed: Trifluoromethanesulfonic acid anhydride (1.00 equivalents) was slowly added to a solution of dibenzo[b,d]thiophene-5-oxide (1.00 equivalents) in dry dichloromethane (10 mL/mmol) at −50° C. The reaction mixture was stirred at −50° C. for 1 h, then trimethylsilyl cyanide (1.00 equivalents) was added dropwise at −50° C. The reaction mixture was stirred at −50° C. for another 2 h, then allowed to warm up to room temperature and stirred for 0.5 h at this temperature. The resulting mixture was then filtered under nitrogen pressure and the solid residue was washed three times with dry dichloromethane (3×5 mL/mmol) and dried under high vacuum to remove solvent residue. The desired product was obtained as white powder. $^1$H NMR (300 MHz, CD$_3$CN) δ 8.56 (dd, J=8.4, 0.9 Hz, 2H), 8.35 (dd, J=7.8, 1.2 Hz, 2H), 8.04 (td, J=7.5, 1.2 Hz, 2H), 7.89-7.83 (m, 2H); $^{13}$C NMR (75 MHz, CD$_3$CN) δ 141.71, 137.18, 133.70, 129.98, 127.24, 126.40, 121.87 (q, $^1J_{C-F}$=318.5 Hz), 103.87. m/z calculated by HRMS (high resolution mass spectrometry) for C$_{13}$H$_8$NS$^+$[M-OTf$^-$]: [M-OTf-]: 210.0372, found (ESI) 210.0365.

Figure 6B:
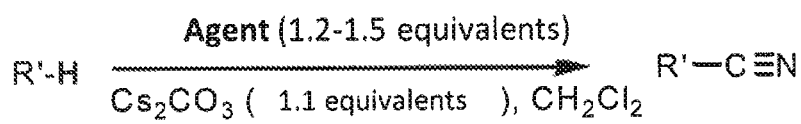
Figure 6B:
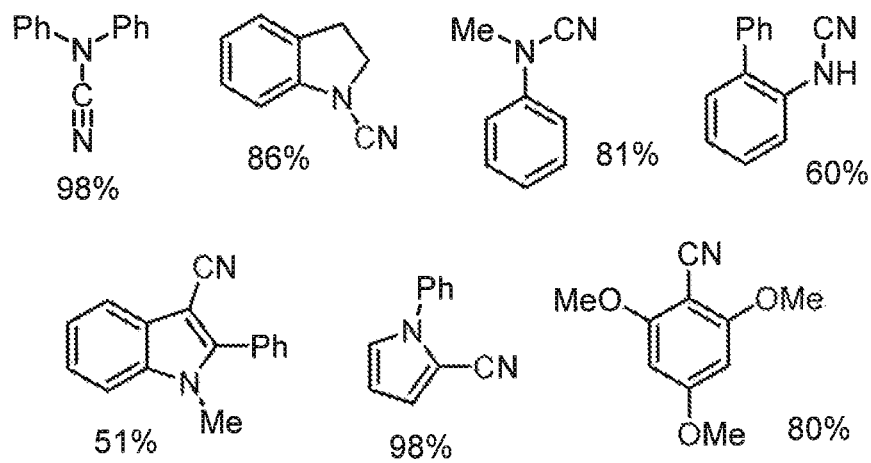

FIG. 6b shows the yields of the cyanation reactions.

The invention is explained in more detail below with reference to the figures:

The approach according to the invention is based on the reaction of dibenzothiophene 4 (see scheme in FIG. 1) with hydrogen peroxide in the presence of e.g. trifluoromethanesulfonic acid (Tf-OH) to obtain the corresponding S-oxide 5, which subsequently leads to an orange suspension of bistriflate 6 in a reaction with e.g. one equivalent of trifluoromethanesulfonic acid anhydride (see also Fascione et al., Chem. Eur, 12012, 18, 2987-2997). Bistriflate 6 can then be reacted, for example, by adding a TMS (trimethylsilane)-protected alkyne to the reaction mixture, which resulted in a slow formation of a slightly yellow solution of 5-(alkynyl)dibenzothiophenium triflates 3a-f as white solids after distilling off the solvent and washing with dry diethyl ether (Et$_2$O) (see FIG. 1). The syntheses could be performed on a multigram scale and showed good to excellent yields. Diagnostic features of the compounds 3a-f are low field shifted $^{13}$C-NMR signals of the alkyne carbon atom, the beta carbon to the sulfur being more strongly shifted to the low field (105-110 ppm) and the alpha carbon atom being found at δ=63-69 ppm, the acetylene at δ=73.2 ppm.

EXAMPLES

Nuclear Magnetic Resonance (NMR) experiments $^{13C}$-NMR spectra were recorded in deuterated chloroform (CDCl$_3$) and deuterated DCM (CD$_2$Cl$_2$) (Bruker AV300 and Bruker AV500).

Cited Literature:

Fascione et al., Chem. Eur. J. 2012, 18, 2987-2997.

Höfer et al., J. Pol. Sci: Part A: Pol. Chem. 2009, 47, 3419-3430.

Ochiai, et al., Org. Biomol. Chem. 2003, 1, 1517-1521.

Talavera et al.: "Dihalo(imidazolium)sulfuranes: A Versatile Platform for the Synthesis of New Electrophilic Group-Transfer Reagents", J. Am. Chem. Soc. 2015, 137, 8704-8707.

Zhdankin et al.: "1-(Organosulfonyloxy)-3(1H)-1,2-benziodoxoles: Preparation and Reactions with Alkynyltrimethylsilanes", J. Org. Chem 1996, 61, 6547.

WO 2017/001245 A1

WO 2016/107578 A1

WO 2016/087879 A1

The invention claimed is:

1. A salt containing a compound of formula I or II:

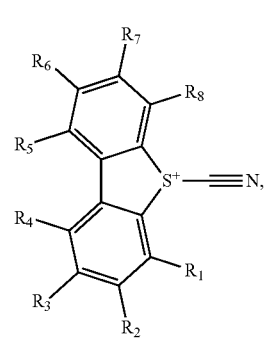

-continued

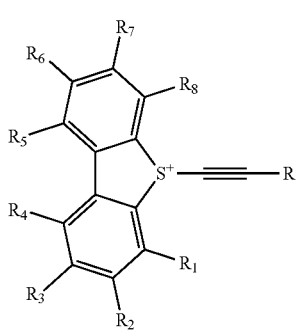

II wherein $R_1$-$R_8$ are independently selected from the group consisting of: H, Cl, Br, F, I, $NO_2$, O—$C_{1-6}$ alkyl, $SO_3^-$, $C_{1-6}$ alkyl, $C_{6-12}$ aryl, $C_{6-12}$ aryl, $C_{6-12}$ heteroaryl, CN, COOR*, where R*=H, $C_{1-6}$ alkyl, $C_{6-12}$ aryl, and COO—;

wherein R in Formula II is selected from the group consisting of: H, OMe, silyl groups and optionally substituted $C_6$ aryl groups, optionally substituted $C_{3-12}$ cycloalkyl groups, optionally substituted $C_{1-20}$ alkyl groups.

2. The salt according to claim 1, wherein R is an $R'_3$ silyl group, wherein the three R' substituents are independently selected from the group consisting of: optionally substituted linear, branched or cyclic $C_{1-12}$ hydrocarbon groups optionally having one or more unsaturated bonds and optionally one or more heteroatoms.

3. The salt according to claim 1, wherein R and the three R' substituents of the $R'_3$ silyl group are independently selected from the group consisting of: optionally substituted $C_{4-12}$ cycloalkenyl groups having one or more unsaturated C—C double bonds, optionally substituted $C_{6-12}$ aryl groups, optionally substituted $C_{3-12}$ cycloalkyl groups, optionally substituted $C_{1-20}$ alkyl groups, optionally substituted $C_{1-20}$ alkenyl groups having one or more unsaturated C—C double bonds, optionally substituted $C_{1-20}$ alkynyl groups, optionally substituted $C_{1-20}$ heteroalkyl groups, optionally substituted $C_{1-20}$ heteroalkenyl groups having one or more unsaturated double bonds, optionally substituted $C_{1-20}$ heteroalkynyl groups optionally having one or more unsaturated bonds, optionally substituted $C_{6-12}$ heteroaryl groups, optionally substituted $C_{3-12}$ heterocycloalkyl groups, optionally substituted $C_{3-12}$ heterocycloalkenyl groups having one or more unsaturated double bonds.

4. The salt according to claim 1, wherein the compound of formula I or formula II represents the cation and the anion is selected from the group consisting of: triflate (TfO$^-$); perchlorates; nitrate; $Tf_2N$; [{3,5-$(CF_3)_2C_6H_3$}$_4$B]$^-$; PF6$^-$; BF4$^-$; B($C_6F_5$)$_4^-$; BF$_4^-$; BR*$_4$, wherein R* is optionally substituted $C_{1-6}$ alkyl, or optionally substituted $C_{6-12}$ aryl; 1-carba-closo-dodecaborate(1-) and corresponding compounds; HC($SO_2CF_3$)$_2^-$ and corresponding compounds; $C_{60}^-$; halides; SbF$_6^-$; Sb$_2$F$_{11}^-$ and antimonate compounds; fluorinated alkoxyaluminates; and tosylates.

5. The salt according to claim 1 wherein R is selected from phenyl, toluene, para-methoxyphenyl, naphthyl, triisopropylsilyl, triethylsilyl, trimethylsilyl, tent-butyl dimethylsilyl and tent-butyl diphenylsilyl.

6. A cyanation or alkynylation reaction comprising the steps
a) providing a salt containing the compound of formula I or II:

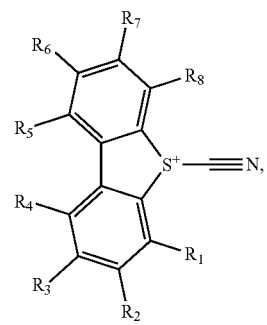

I

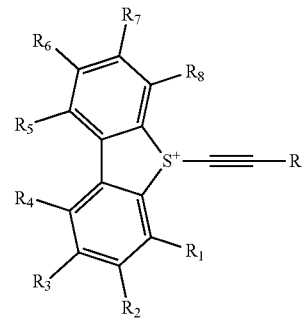

II wherein $R_1$-$R_8$ are independently selected from the group consisting of: H, Cl, Br, F, I, $NO_2$, O—$C_{1-6}$ alkyl, $SO_3^-$, $C_{1-6}$ alkyl, $C_{6-12}$ aryl, O—$C_{6-12}$ aryl, $C_{6-12}$ heteroaryl, CN, COOR*, where R*=H, $C_{1-6}$ alkyl, $C_{6-12}$ aryl, and COO$^-$;

wherein R in Formula II is selected from the group consisting of: H, OMe, silyl groups and optionally substituted $C_6$ aryl groups, optionally substituted $C_{3-12}$ cycloalkyl groups, optionally substituted $C_{1-20}$ alkyl groups; and b) reacting the salt with a nucleophile (Nu).

7. The cyanation or alkynylation reaction according to claim 6, wherein step a) further comprises
a') Providing a compound of formula III

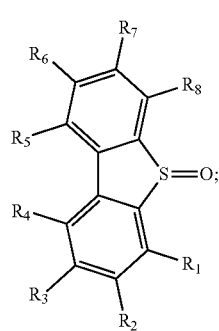

III and reacting the compound of formula III to a salt containing the compound of formula I or II in two reaction steps:

Step 1) reacting with an acid anhydride or an ester; and
Step 2) subsequent reaction with a reagent selected from the group consisting of:

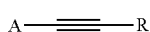

or A-CN, where A is selected from cations, ZnX, MgX, where X=halogen; TMS; $BR_2$ and $BR_3^-$, where R=optionally fluorinated O—$C_{1-6}$ alkyl, optionally fluorinated $C_{1-6}$ aryl, F or H.

8. The cyanation or alkynylation reaction according to claim 7, wherein step a') further comprises
a") providing a compound of formula IV

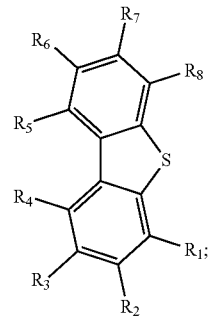

and reacting the compound of formula IV to the compound of formula III by reaction with an oxidizing agent, wherein $R_{1-8}$ are independently selected from the group consisting of: H, Cl, Br, F, I, $NO_2$, O—$C_{1-6}$ alkyl, $SO_3^-$, $C_{1-6}$ alkyl, $C_{6-12}$ aryl, O—$C_{6-12}$ aryl, $C_{6-12}$ heteroaryl, CN, COOR*, where R* =H, $C_{1-6}$ alkyl, $C_{6-12}$ aryl, and COO—.

9. The cyanation or alkynylation reaction according to claim 6, wherein the nucleophile is selected from the group consisting of $R^x$—H, $R^x$—S—H, $R^x_2$—N—H, $R^x$—C(O)S—H, $R^x$—C(O)NR$^x$—H, sulfonamides ($R^x$—S(O)$_2$NR$^x$—H), doubly activated methylene compounds, amides, electron-rich aromatics, nitrogen-containing $C_{5-12}$ heterocycles, and $Ph_3P$, wherein $R^x$ is selected from the group consisting of: optionally substituted linear, branched or cyclic $C_{1-30}$ hydrocarbon groups optionally containing one or more unsaturated bonds and optionally one or more heteroatoms.

10. The salt according to claim 1 containing the compound having the formula

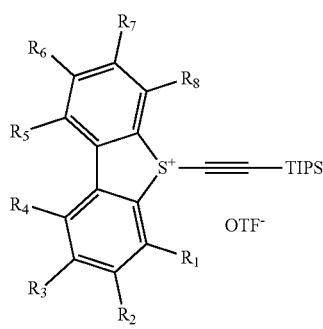

where TIPS stands for triisopropylsilyl.

11. The salt according to claim 1 containing the compound having the formula

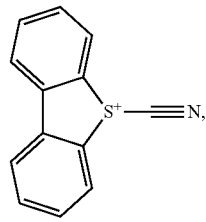

I

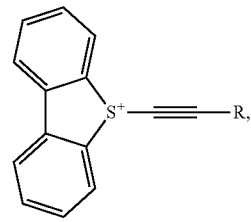

II wherein R is triisopropylsilyl and the anion is triflate (TfO$^-$) in formula I and II.

12. The method of claim 6, wherein in step b) reacting the salt with a nucleophile (Nu) is performed in the presence of a base or a Lewis acid.

13. The method of claim 6, wherein in step b) reacting the salt with a nucleophile (Nu) is performed in the presence of a base or a Lewis acid, wherein the compound of formula I is used, wherein —CN or the compound

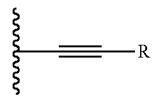

binds to the nucleophile.

14. The salt according to claim 1 containing the compound having the formula

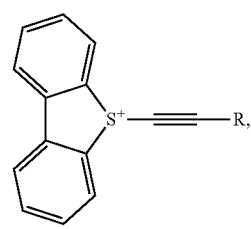

II wherein R is para-substituted phenyl.

* * * * *